United States Patent [19]

Szabó Anna Z. et al.

[11] Patent Number: 5,380,761
[45] Date of Patent: Jan. 10, 1995

[54] TRANSDERMAL COMPOSITIONS

[75] Inventors: Szabó Anna Z.; Gabriella Szabó née Ujhelyi; Antal Tóth; Tamás Szüts; Kálmán Magyar; József Lengyel; János Pintér; Anna Székely; András Szego, all of Budapest; Katalin Mármarosi née Kellner, Biatorbágy, all of Hungary

[73] Assignee: Chinoin Gyogyszer- ES Vegyeszeti Termekek Gyara RT., Budapest, Hungary

[21] Appl. No.: 140,279

[22] Filed: Oct. 20, 1993

Related U.S. Application Data

[63] Continuation of Ser. No. 861,537, Apr. 1, 1992, abandoned.

[30] Foreign Application Priority Data

Apr. 15, 1991 [HU] Hungary ............... 1229/91

[51] Int. Cl.6 ............................................. A61K 31/135
[52] U.S. Cl. .................................... 514/655; 424/449
[58] Field of Search ........................ 514/655; 424/449

[56] References Cited

U.S. PATENT DOCUMENTS

| | | | |
|---|---|---|---|
| 4,861,800 | 8/1989 | Buyske | 514/546 |
| 4,868,218 | 9/1989 | Buyske | 514/646 |
| 5,053,227 | 10/1991 | Chiang et al. | 424/448 |
| 5,096,612 | 3/1992 | Pinter et al. | 252/299.01 |

FOREIGN PATENT DOCUMENTS

0099302A2  7/1983  European Pat. Off. .
WO89/09051 10/1989 WIPO .

OTHER PUBLICATIONS

New Nematic Phase In Lyotropic Binary Liquid Crystals Detected By Position Annihilation Techniques–1986, vol. 136, pp. 153–166.
Die Pharmazeutische Industrie, Pharm. Ind. 40,3, pp. 256–261 (1978).
Arch Gen Psychiatry–vol. 44, May 1987; pp. 427–433; P. N. Tariot et al; 'L–Deprenyl in Alzheimer's Disease'.
Psychopharmacology (1987) 91, pp. 489–495; P. N. Tariot et al 'Cognitive effects of L–deprenyl in Alzheimer's disease'.
Clinical Neuropharmacology; vol. 13, No. 2. pp. 147–163 (1990) 'Neuropsychological Effects of L–Deprenyl in Alzheimer's Type . . . '.
Pharmacopsychiat, 20 (1987) pp. 256–257; E. Martini et al 'Brief Information on an Early Phase–II–Study With Deprenyl . . . '.
Journal of Controlled Release, 13 (1990) pp. 73–81; Tiemessen et al; 'Probing the Microstructure of Liquid Crystalline Surfactant . . . '.
Biochemical Pharmacology, 1963, vol. 12; pp. 1417–1419; R. J. Wurtman et al; 'Sex Steroids, Cardiac H–Norepinephrine . . . '.
Medical Biology vol. 54; pp. 137–141; (1976) A. Wiberg (List continued on next page.)

*Primary Examiner*—James H. Reamer
*Attorney, Agent, or Firm*—Herbert Dubno; Jonathan Myers

[57] ABSTRACT

An anhydrous transdermal composition is disclosed comprising in a 20 to 100% lyotropic liquid crystalline arrangement:

5 to 15 weight % of optically active or racemic N-methyl-N-(1-phenyl-2-propyl)-2-propynylamine or N-methyl-N-{1-(4-fluorophenyl)-2-propyl}-2-propynylamine or a pharmaceutically acceptable salt thereof;

40 to 70% by weight of liquid polyethylene glycol;

10 to 20% by weight of solid polyethylene glycol;

2 to 30% by weight of a nonionic surface active agent;

2 to 20% by weight of propylene glycol, and if desired, 0.5 to 2% by weight of a polymer, the a value of which is greater than 0.6, and optionally, in an amount needed up to 100% an emulsifying agent.

6 Claims, No Drawings

OTHER PUBLICATIONS et al 'Quantitative Aspects On Mitochondrial Monoamine Oxidase In . . . '.
Muszaki Konyvkiado 1986, pp. 107–110.
Merck Index, 10th Ed., Compounds 7545, 7555.
Sigma Catalog of Biochemicals and Organic Compounds, p. 290 (1992).
Cremophor ® EL, BASF.
Myritol 318ʳ, Henkel.
Science; vol. 245; pp. 519–522, Aug. 4, 1989; James W. Tetrud and J. M. Langston; 'The Effect of Deprenyl (Selegiline) on the . . . '.
New England Journal of Medicine; Nov. 16, 1989; pp. 1364–1371; 'Effect of Deprenyl On the Progression of Disability In Early . . . '.
Acta Neurol Scand 1983: Suppl 95; pp. 103–105; W. Birkmayer; 'Deprenyl (selegiline) in the treatment of Parkinson's disease'.

TRANSDERMAL COMPOSITIONS

This is a continuation of co-pending application Ser. No. 07/861,537 now abandoned filed on Apr. 1, 1992.

SPECIFICATION

1. Field of the Invention

The invention relates to an anhydrous transdermal composition, containing the active ingredient and the auxiliary materials in a 20–100% lyotropic liquid crystalline arrangement.

2. Background of the Invention

In the case of certain therapeutical active ingredients it is well known that application in a transdermal form has its advantages. Depending on the release constant of the active ingredient from the transdermal composition the required amount of active ingredient to treat a given disease and the active ingredient release assuring constant blood level can be ensured for a period of 1 day to 1 week.

It is known from the literature, that the monoamine oxidase-B and dopamine reuptake inhibiting compound Deprenyl can be successfully applied to slow down the development of Parkinson's disease in human subjects at early stages of the disease (Tetrud J W, Langston J V.: The effect of Deprenyl (Selegiline); The natural history of Parkinson's disease, Science 1989., 245 514–522.; The Parkinson Disease Study Group: Effect of Deprenyl on the progression of disability in early Parkinson disease, N. Engl. J. Med. 1989. 321 1364–71). It administered in combination with L-Dopa containing preparations in the late phase of Parkinson's disease (Birkmayer:Deprenyl (Selegiline) in the treatment of Parkinson's disease. Acta Neurologica Scand. 1983 Supp. 95 103–106). It is useful in certain cases of schizophrenia (published PCT application No. 90/01298/and according to the latest test results in dementia of Alzheimer type (Pierre N. Tariot, MD., Robert M. Coken MD. PhO, Trey Sunderland M.D.: 1-Deprenyl in Alzheimer's disease. Arch. Gent. Psychiatry Vol. 44. May 1987; P. N. Tarlot, T. Sunderland: Cognitive effects of 1-Deprenyl in Alzheimer's disease: Psychopharmacology (1987) 91: 489–495; Gian Luigi Piccini, Giancarlo Finali, Massimo Piccirilli: Neuropsychological Effects of 1-Deprenyl in Alzheimer's type Dementia. Clinical Neuropharmacology Vol. 13, No. 2. pp. 147–163; E. Martiny, I. Pataky, K. Szilagyi, V. Ventor: Brief Information on an early phase II. Study with Deprenyl in demented patients Pharmacopsychiatr. 20 (1987) 256–257.)

U.S. Patent Nos. 4,868,218 and 4,861,800 and PCT patent specification WO No. 89/09051 describe the possibility of transdermal application of Deprenyl. According to the disclosure of these patent documents, any known, usually applied liquid or solid transdermal basic system is suitable for the transdermal administration of Deprenyl.

Studying the compositions published in the above mentioned literature, other traditionally applied o/w emulsifying ointment bases, w/o emulsifying ointment bases and hydrogels respectively, we have found that the active ingredient was not absorbed at all, or was absorbed completely within some hours.

OBJECT OF THE INVENTION

We set it is an object of our invention to provide a dermal preparation which assures a sufficient and uniform release of the active ingredient for at least 24, advantageously for 72 hours, to treat the disease.

DESCRIPTION OF INVENTION

It is known further, that some surface active agents are applied in transdermal basic ointments, e.g. decaethyloxide-oleylether (Brigj 96) to form a liquid crystalline system with water. In these creams the polyethyleneoxide chain of the surface active agent and the water form a continous hydrophilic area, which plays a well-defined role in the diffusion of the active ingredient.

By varying the water surface active agent ratio the liquid crystalline system and thereby the active ingredient diffusion can be influenced. (Journal of Controlled Release, 13 (1990) 73–81).

Surprisingly we have found, that in the case of a suitable composition even in an anhydrous medium a lyotropic liquid crystalline system can be formed. By varying the quantity of some components the particle size of the liquid crystals, and the ratio of the liquid crystalline arrangement compared to the total system can be influenced. In that way transdermal systems, ensuring uniform active ingredient release for 24, 48 and 72 hours, corresponding to the therapeutic demand, can be prepared.

According to the aboves, the present invention relates to an anhydrous transdermal composition containing in a 20–100% lyotropic liquid crystalline arrangement:

- 1–30 w. % of optically active or racemic N-methyl-N-(1-phenyl-2-propyl)-2-propynylamine (hereinafter Deprenyl), or N-methyl-N-(1-(4-fluorophenyl)-2-propyl)-2-propinyl-amine or the therapeutically suitable salts of them,
- 40–70 w. % of liquid polyethyleneglycol,
- 10–20 w. % of solid polyethyleneglycol,
- 2–30 w. % of a nonionic surface active agent,
- 2–20 w. % of propyleneglycol, if desired
- 0.5–2 w. % of a polymer the a value of which is $>0.6$, and if desired other auxiliary agents-needed to 100 w. %, as emulsifying agents.

As liquid polyethyleneglycol in the composition polyethyleneglycol 200–600, preferably polyethyleneglycol 400 and as solid polyethyleneglycol, polyethyleneglycol 1500–6000, preferably polyethyleneglycol 4000 can be used. For non ionic surface active agent e.g. polyethyleneglycol-fatty-acid-ethers, polyethyleneglycol-fatty-acid-alcohols, polyethyleneglycol-fatty-acid-esters, sorbitan-fatty-acid-esters, polyethyleneglycol-castor-oils, preferably polyethyleneglycol-fatty-acid-ethers can be used.

As another auxiliary material, as for example as emulsifying agent, polysaccharide can be used.

As a polymer this agent can have a coilness characterizing a value of which is $>0.6$, for example polyethyleneglycol 35.000.

The coilness i.e. permeability of the polymer, can be characterized by the a exponent of the Kuhn, Mark, Honwick equation describing relation between frontviscosity and molecular mass (see: Rohrsetzer S., Kolloidika, Tankönyvkiadó 1986, D. J. Shaw: Introduction to colloid and surface chemistry, Me,uml/u/ szaki Könyvkiadó 1986, in Hung.).

The composition according to the invention can be prepared as follows: Warming up the liquid polyethyleneglycol, adding the solid polyethyleneglycol in melted form, then adding the surface active material and active ingredient warm dissolved in polyethylene glycol, cooling the mixture and adding the polymer and if desired the other auxiliary agents.

HPLC we have found quickly, respectively slowly absorbable active ingredient containing ointments. The results are shown in Table II.

TABLE I

Effect of Deprenyl (1 mg/kg s.c.) and UG85 Deprenyl-plaster (3 mg/kg) on the inhibition of MAO-B activity (%) as compared to the control. Measurements were made in rat brain- and liver nucleus free homogenates with $^{14}$dC-PEA substrate. ±S.D. (n = 9[x])

| time | brain | | liver | |
|---|---|---|---|---|
| | s.c. | plaster | s.c. | plaster |
| 0' | 0 | 0 | 0 | 0 |
| 5' | — | 9.6 ± 6.86 | — | 0 |
| 15' | — | 45.07 ± 13.72 | — | 14.23 ± 20.80 |
| 30' | — | 60.60 ± 3.84 | — | 12.80 ± 15.25 |
| 45' | — | 66.91 ± 1.88 | — | 45.10 ± 10.48 |
| 1 hour | 79.02 ± 1.58 | 73.09 ± 5.05 | 63.23 ± 11.98 | 58.93 ± 19.08 |
| 2 hours | 87.09 ± 2.05 | 53.22 ± 3.42 | 74.94 ± 1.10 | 69.63 ± 6.94 |
| 4 hours | 86.74 ± 3.00 | 55.30 ± 2.96 | 57.63 ± 5.23 | 52.80 ± 9.29 |
| 6 hours | 83.04 ± 1.46 | 41.49 ± 3.50 | 67.86 ± 9.22 | 57.06 ± 4.68 |
| 24 hours | 89.36 ± 2.60 | 80.50 ± 3.24 | 86.04 ± 7.81 | 80.19 ± 3.74 |
| 48 hours | 73.59 ± 1.77 | 72.05 ± 2.54 | 64.34 ± 8.11 | 86.65 ± 2.26 |
| 72 hours | 76.99 ± 3.38 | 76.56 ± 1.13 | 68.54 ± 5.25 | 79.09 ± 2.59 |
| 96 hours | 69.19 ± 3.58 | 56.00 ± 2.37 | 54.75 ± 11.58 | 65.59 ± 7.04 |
| 7 days | 32.20 ± 5.45 | 32.15 ± 12.49 | 56.44 ± 7.59 | 55.33 ± 11.69 |
| 9 days | 13.56 ± 1.97 | 18.16 ± 5.22 | 44.26 ± 3.45 | 47.66 ± 5.43 |
| 11 days | 0.63 ± 0.95 | 14.88 ± 2.92 | 26.27 ± 15.77 | 39.18 ± 4.34 |
| 14 days | 0 | 0 | 24.22 ± 3.13 | 0 |

[x]: 3 animals and 3 parallel measurements at a given time

The active ingredient applied in the composition can be prepared according to the European specifications No. 0186680 and 0099302.

The abovementioned transdermal composition is applied in the treatment on the skin surface in the required dose. thereafter the treated surface is covered, e.g. with plaster.

Because of the low dose-demand (5–10 mg/day) of the active ingredient we could not determine the blood-level directly, therefore we determined it partly indirectly by a biochemical method determining the monoamine-oxidase (MAO) inhibiting effect of the active ingredient in the brain and liver tissues, and partly from the quantity of the unabsorbed active ingredient from the plaster by HPLC.

The aim of these studies was to determine absorption parameters of the transdermal preparations of different composition. As a model, rats and beagle clogs depilated on the required surface were used. The absorption kinetic was followed by determining the quantity of the unabsorbed active ingredient (HPLC). Besides we measured the monoamine oxidase (MAO) inhibiting effect of the absorbed active ingredient in rat brain and liver tissues.

Test methods: MAO activity of rat brain and liver tissues was determined by the radiometric method of Wurtman and Axelrod (Biochem. Pharmacol. 1963. 12, 1417). The remaining active ingredient content of the plasters removed from the test animals was determined by HPLC. The numerical results were obtained by calibration prepared from different quantities of an ointment.

Results and evaluation of the data: In rat studies the extent of monoamine oxidas-B enzyme inhibition shows that the active ingredient missing from the plaster determined by HPLC was absorbed. Table I contains the results of these measurements.

The absorption velocity measured on rat skin shows that the skin of rats is not suitable as a kinetic mode, since most of the preparations are absorbed within 1 hour. A more suitable model is the beagle dog. In this case by measuring the remaining active ingredient by

TABLE II

Transdermal absorption of Deprenyl in beagle dogs

| Ointment | Duration of experiment (hours) | Remaining Deprenyl % ±S.D. |
|---|---|---|
| Ug 85 | 24 | 9.6 ± 1.5 |
| Ug 110 | 24 | 34.9 ± 15.3 |
| Ug 111 | 24 | 1.7 ± 2.2 |
| Ug 118 | 24 | 13.4 ± 6.6 |
| Ug 167[x] | 4 | 75.7 ± 6.8 |
| Ug 167[x] | 24 | 40.6 ± 4.9 |
| Ug 325 | 24 | 58.5 ± 4.1 |
| Ug 325 | 48 | 28.3 ± 12.1 |
| Ug 325 | 72 | 8.4 ± 2.4 |

In further experiments we determined in domestic pigs The MAO activity in the brain and the platelet MAO-B activity.

The experiments were carried out on female (big white) domestic pigs, weighing 25–30 kg. The pigs were caged separately during the experiments, and the same food was supplied, which was used formerly.

Animals in the first group were treated orally with 10 mg of (—)-deprenyl in a gelatinous capsule. Blood samples were taken for the determination of MAO-B activity at: 0, 3, 6, 24, 48, 72 and 96 h. At 96 h after blood sampling the pigs were killed and the MAO-B and MAO-A activity was determined in their dissected brain.

The second group was treated with the UG-111 transdermal preparation containing 10 mg (—)-deprenyl. The times of blood sampling were at: 0, 3, 6, 24 and 48 h. The transdermal preparations were removed at 24 h. For the determinations of the residual (—)-deprenyl content of the preparations the patch and its nylon cover were used. The skin was washed with ethanolic cotton - wool, which was also used for HPLC determination. The pigs were killed at 48 h and MAO-A and MAO-B activity of the brain was determined.

The third group of the pigs was treated with UG-167 containing 20 mg of (—)-deprenyl. Blood samples were taken at: 0, 3, 6, 24, 48 and 72 h. The patches were removed at 48 h and the whole procedure described at group 2 was accomplished.

The blood was taken from the v. cava cranialis with a 20 ml plastic syringe containing 1.5 ml 7.6% Na-citrate solution. The volume of the blood taken was 18.5 ml at every time of sampling.

MAO activity was measured radiometrically according to the methods of Wurtman and Axelrod (Biochem. Pharmacol. 12. 1414–19; 1963) with a slight modification (K. Magyar in: Monoamine Oxidases and their Selective Inhibition. Ed.: K. Magyar, Pergamon Press, Akadémiai Kiadó, Budapest 11–21; 1980).

The method described by Willberg and Oreland was followed for platelet preparation (Med. Biol., 54: 137–44; 1976).

The results of the inhibition of MAO-B activity of the platelet after p. os and transdermal application are shown in Table III.

TABLE III

Effect of (−)-Deprenyl on the inhibition of MAO-B
actvity of the platelets (%) as compared to the control.
Measurements were made with $^{14}$DC-PEA substrate ±S.D. (n = 3)

| mode of application | time | | | | |
|---|---|---|---|---|---|
| | 3 | 6 | 24 | 48 | 72 |
| 1 | 97.77 | 86.04 | 100.00 | 82.67 | 72.32 |
| per os | 92.52 | 96.51 | 100.00 | 70.48 | 65.63 |
| (10 mg) 0.0 | 95.63 | 100.00 | 69.93 | 50.17 | |
| | 95.15 | 92.73 ± 3.35 | 100 ± 0.0 | 74.36 ± 4.16 | 52.71 ± 6.56 |
| 2 | 0.0 | 36.27 | 52.68 | 60.70 | |
| UG-111 | 54.80 | 86.47 | 86.02 | 92.03 | — |
| trans- | 95.66 | 95.47 | 93.76 | 98.63 | — |
| dermal | 75.23 | 72.74 ± 18.42 | 77.49 ± 12.6 | 83.79 ± 11.7 | |
| (10 mg; 24 h) | | | | | |
| 3 | 23.29 | 55.77 | 90.94 | 88.56 | 100.00 |
| UG-167 | 72.11 | 95.90 | 98.54 | 91.44 | 89.34 |
| trans- | 65.81 | 65.05 | 0.0 | 90.57 | 75.02 |
| dermal | 53.74 ± 15.33 | 72.24 ± 12.13 | 94.74 | 90.19 ± 0.85 | 88.12 ± 7.24 |
| (20 mg; 48 h) | | | | | |

The results of the determination of MAO activity in the brain are shown in Table IV.

TABLE IV

Effect of (−)-Deprenyl on the inhibition of MAO-activity
(%) as compared to the control. Measurements were
made in domestic pig brain nucleous free homogenates with
$^{14}$C-PEA; $^{14}$C-5-HT substrate. ±S.D. (n = 3)

| mode of application | brain | |
|---|---|---|
| | $^{14}$C-PEA | $^{14}$C-5-HT |
| p. os (96 h) | 73.22 ± 8.13 | 20.14 ± 6.0 |
| UG-111 (48 h) transdermal (24 h) | 56.31 ± 10.03 | 16.39 ± 8.77 |
| UG-167 (72 h) transdermal (48 h) | 86.76 ± 6.67 | 18.50 ± 3.81 |

In table V. the transdermal absorption is shown.

TABLE V

Transdermal absorption of Deprenyl in domestic
pigs as compared to the control.

| preparation | Duration of experiments (hours) | Remaining Deprenyl % ±S.D. |
|---|---|---|
| UG-111 | 24 | 14.2 ± 5.5 |
| UG-167 | 24 | 36.5 ± 9.3 |
| UG-167 | 48 | 6.1 ± 5.1 |

The composition, particle size, the percentage of liquid crystalline state of the different preparations was as follows:

UG-85
| | |
|---|---|
| Polyethylene glycol (PEG) 4000 | 60.0 g |
| PEG 200 | 100.0 g |
| Propyleneglycol | 30.0 g |
| Deprenyl | 3.0 g |
| PEG 400 ad | 300.0 g |

Average particle size: 9 micron; liquid crystalline state: 28%.

UG-111
| | |
|---|---|
| PEG 4000 | 16.0 g |
| PEG 400 | 60.0 g |
| Propyleneglycol | 8.0 g |
| CREMOPHOR EL ® | 2.0 g |
| Deprenyl | 5.0 g |
| PEG 400 ad | 100.0 g |

Average particle size: 72.7 microns; liquid crystalline state: 20%.

UG-118
| | |
|---|---|
| PEG 4000 | 16.0 g |
| PEG 400 | 60.0 g |
| Propylene glycol | 8.0 g |
| CREMOPHOR EL ® | 2.0 g |
| Deprenyl | 5.0 g |
| MYRITOL 318 ® | 3.0 g |
| PEG 400 ad | 100.0 g |

Average particle size: 36.4 microns; liquid crystalline state: 50%.

UG-110
| | |
|---|---|
| PEG 4000 | 15.0 g |
| PEG 400 | 60.0 g |
| Propyleneglycol | 10.0 g |
| Deprenyl | 5.0 g |
| CREMOPHOR EL ® | 5.0 g |
| PEG 400 | 5.0 g |

UG-167
| | |
|---|---|
| PEG 4000 | 19.0 g |
| PEG 400 | 55.0 g |
| Propyleneglycol | 8.0 g |
| Xanthan gum | 10.0 g |
| Deprenyl | 5.0 g |
| PEG 400 ad | 100.0 g |

Average particle size: 91–109 microns; liquid crystalline state: 70–80%

UG-325
| | |
|---|---|
| PEG 35.000 | 1.0 g |
| PEG 4000 | 15.0 g |
| PEG 400 | 53.5 g |
| Propyleneglycol | 4.5 g |
| Xanthan gum | 15.0 g |
| Deprenyl | 5.0 g |
| CREMOPHOR EL ® | 6.0 g |

Liquid crystalline state: 100%.

Composition of the auxiliary-agents:

CREMOPHOR EL$^R$: glycerin-polyethyleneglycol-ricinoleate

MYRITOL 318$^R$: triglyceride

Xanthan gum: polysaccharide

CHREMOPHOR EL$^R$

Emulsifier for the pharmaceutical and cosmetic industries, as well as for the feed industry for the production of aqueous preparations of hydrophobic substances, e.g. fat-soluble vitamins, etheric oils, etc.

Polyoxyethylenglycerotriricinoleat 35 (DAC), Polyoxyl Castor oil (USP/NF).

Character: CREMOPHOR EL$^R$ is a non-ionogenic solutizer and emulsifier, prepared by treating Castor Oil (1 mole with Ethylene Oxide (35 Mol). The starting materials is Castor Oil with DAB-8 quality.

The main component of Cremophor EL is glycerine polyoxyethylene ricine oleate This together with the fatty acid polyoxyethylene esters constitute the hydrophobic part of the product. The smaller hydrophilic part consists of polyethylene glycols and glycerine ethologist.

Cremophor EL$^R$ is a light yellow, oily liquid, clear above 26° C., with a weak but characteristic odor. When heated, the last solid parts liquefy by 26° C. The HLB-value ranges between 12 and 14.

| | |
|---|---|
| Viscosity according to Höpplet at 25° C. | 700–800 cP |
| Density at 25° C. | 1.05–1.06 g/ml |
| Refractive Index at 25° C. | 1.465–1.475 |
| Saponification value | 63–72 |
| Hydroxyl number | 65–78 |
| Iodine number | 28–32 |
| Acidity (Mineral acidity?) | $\leq 2$ |
| Water content according to K. Fischer | $\leq 3\%$ |
| pH-value of the 10% aqueous solution | 6–8 |
| Sulfate ash | $\leq 0.2\%$ |
| Heavy metals /USP XX/ | $\leq 10$ ppm. | composition:

Capryl/Capric acid-Triglyceride

Nature of the product

MYRITOL 318$^R$ is a neutral, almost colorless, odorless, clear oil with low viscosity.

| Characteristic data | |
|---|---|
| Mineral acidity | below 0.1 |
| Saponification value | 340–350 |
| Iodine number | approx. 0.5 |
| Hydroxyl number | below 5 |
| Refractive index (20° C.) | 1.448–1.450 |
| Turbidity point | below −5° C. |
| Solidifying point | below −10° C. |
| Density (20° C.) | 0.945–0.947 g/cm$^3$ |
| Viscosity (20° C.) | 25 31 mPa · s |

Properties and Use

MYRITOL 318$^R$ is a triglyceride of specially selected saturated vegetal fatty acids which is particularly suitable to oil bodies of this type. Due to its chemical composition and its neutral character MYRITOL 318 is a particularly skin-friendly oil component. The low content of unsaturated substance (Iod number approx. 0.5) as well as its low acidity (under 0.1) result in an exceptional stability. It can be mixed with many solvents e.g. Ethyl - and Isopropyl alcohol, chloroform, glycerin, etc. and besides it has very good solubility in many lipoid-soluble substances used in the cosmetic field.

What we claim is:

1. A process for the preparation of an anhydrous transdermal composition comprising in a 20 to 100% lyotropic liquid crystalline arrangement:

5 to 15 weight % of optically active or racemic N-methyl-N-(1-phenyl-2-propyl)-2-propynylamine or N-methyl-N-{1-(4-fluorophenyl)-2-propyl}-2-propynylamine or a pharmaceutically acceptable salt thereof;

40 to 70% by weight of liquid polyethylene glycol;

10 to 20% by weight of solid polyethylene glycol;

2 to 30% by weight of a nonionic surface active agent;

2 to 20% by weight of propylene glycol, and if desired, 0.5 to 2% by weight of a polymer, the a value of which is greater than 0.6, and optionally, in an amount needed up to 100% an emulsifying agent, which comprises the step of:

(a) preparing a mixture comprising 40 to 70% by weight of the liquid polyethylene glycol, 10 to 20% by weight of the solid polyethylene glycol, 2 to 30% by weight of the non-ionic surface active agent, and 2 to 20% by weight of the propylene glycol;

(b) inoculating the mixture formed in step (a) with 5 to 15% by weight of the optically active or racemic N-methyl-N-(1-phenyl-2-propyl)-2-propynylamine or N-methyl-N-{1-(4-fluorophenyl)-2-propyl}-2-propynylamine or a pharmaceutically acceptable salt thereof dissolved in warm polyethylene glycol; and (c) cooling the inoculated mixture and optionally adding thereto 0.5 to 2% by weight of the polymer, the a value of which is greater than 0.6, to obtain the lyotropic liquid crystalline composition, and adding optionally, in an amount needed up to an emulsifying agent.

2. An anhydrous transdermal composition comprising in a 20 to 100% lyotropic liquid crystalline arrangement:

5 to 15 weight % of optically active or racemic N-methyl-N-(1-phenyl-2-propyl)-2-propynylamine or N-methyl-N-{1-(4-fluorophenyl)-2-propyl}-2-propynylamine or a pharmaceutically acceptable salt thereof;

40 to 70% by weight of liquid polyethylene glycol;

10 to 20% by weight of solid polyethylene glycol;

2 to 30% by weight of a nonionic surface active agent;

2 to 20% by weight of propylene glycol, and if desired, 0.5 to 2% by weight of a polymer, the a value of which is greater than 0.6 , and optionally, in an amount needed up to 100% an emulsifying agent.

3. The anhydrous transdermal composition defined in claim 2 wherein the nonionic surfactant is a polyethylene glycol fatty acid ether, a polyethylene glycol fatty acid alcohol, a polyethylene glycol fatty acid ester, a sorbitan fatty acid ester, or a polyethylene glycol castor oil.

4. The anhydrous transdermal composition defined in claim 6 wherein the polymer, the a value of which is greater than 2 is polyethylene glycol 35,000.

5. A method of treating an animal subject for a disease responsive to inhibiting monoamine oxidase B and to inhibiting dopamine uptake, which comprises applying to the skin of the animal subject, a therapeutically effective amount of the anhydrous transdermal composition defined in claim 2.

6. The anhydrous, transdermal composition comprising a 20 to 100% lyotropic liquid crystalline arrangement, prepared by the process defined in claim 1.

* * * * *